US007306583B2

(12) United States Patent
Goudaliez et al.

(10) Patent No.: US 7,306,583 B2
(45) Date of Patent: Dec. 11, 2007

(54) BAG SYSTEM FOR COLLECTING AND SAMPLING A BIOLOGICAL FLUID

(75) Inventors: Francis Goudaliez, Faches-Thumesnil (FR); Thierry Verpoort, Mouvaux (FR)

(73) Assignee: MacoPharma, Mouvaux (FR)

( * ) Notice: Subject to any disclaimer, the term of this patent is extended or adjusted under 35 U.S.C. 154(b) by 393 days.

(21) Appl. No.: 10/870,618

(22) Filed: Jun. 17, 2004

(65) Prior Publication Data

US 2004/0260265 A1 Dec. 23, 2004

(30) Foreign Application Priority Data

Jun. 20, 2003 (FR) .................................. 03 07493

(51) Int. Cl.
*A61B 19/00* (2006.01)

(52) U.S. Cl. ..................... 604/410; 604/409; 604/411; 604/408; 604/403

(58) Field of Classification Search ................ 604/409, 604/410, 403, 404, 408, 411, 414
See application file for complete search history.

(56) References Cited

U.S. PATENT DOCUMENTS 5,496,301 A * 3/1996 Hlavinka et al. ........... 604/409
6,387,086 B2 5/2002 Mathias et al. ............. 604/409
2004/0009542 A1* 1/2004 Dumont et al. ............ 435/7.32

FOREIGN PATENT DOCUMENTS

EP 1 064 959 A1 1/2001

* cited by examiner

*Primary Examiner*—Jacqueline F. Stephens
(74) *Attorney, Agent, or Firm*—Baker Botts L.L.P.

(57) ABSTRACT

A bag system for the collection and sampling of a biological fluid such as blood is described. The system may include a fluid collection bag and a first tube connected on one end to a collection means and on the other end to the collecting bag. It may also include a flexible sampling bag defining an internal volume having a bottom side and an introduction side which is opposite to the bottom and has an inlet orifice. The system also has a second tube, a first end part of which is connected to the first tube and a second end part of which is inserted in the inlet orifice of the sampling bag, so as to extend inside the sampling bag over a distance of between 25% and 60% of the distance between the bottom and the introduction side of the internal volume of the sampling bag.

6 Claims, 2 Drawing Sheets

3
11
15
14
13
12
1
9
10
6
5
7
2
8
4

BAG SYSTEM FOR COLLECTING AND SAMPLING A BIOLOGICAL FLUID

PRIORITY CLAIM

The present application claims priority under 35 U.S.C. §119(d) to French Application Ser. No. 0307493, filed Jun. 20, 2003.

FIELD OF THE INVENTION

The invention includes a bag system for collecting and sampling a biological fluid, such as blood or a blood component, taken from a donor.

BACKGROUND OF THE INVENTION

Certain bag systems may include a collecting bag intended to receive the blood taken from a donor and intended for transfusion to another person, and a sampling bag intended to receive the first millilitres of blood taken. Both bags are generally flexible, and are formed, for example, from two sheets connected to each other near their periphery.

A first tube is connected at a first end to a collection means, such as a phlebotomy needle intended to be inserted into the arm of the donor, and at a second end to an inlet orifice of the collecting bag.

A second tube is connected at one end to the first tube and at the other end to an inlet orifice of the sampling bag.

A closure system, such as a clamp, is placed on each of the two tubes and makes it possible to direct the blood donated to the sampling bag or to the collecting bag.

A lateral sampling device, connected outside the sampling bag to the second tube, enables the blood contained in the sampling bag to be withdrawn by means of vacuum tubes. The samples of blood thus obtained are normally systematically analysed in order to determine the rhesus group, to make a count and to detect any contaminations such as viruses, bacteria or other undesirable elements present in the blood of the donor, before transfusing the blood to another person.

Filling the sampling bag prior to the collecting bag presents a certain number of advantages and improves the quality of the samples and the blood remaining for transfusion.

First, this reduces the risk of contamination of the blood intended for transfusion. Such contamination often results from the presence of bacteria or other foreign substances on the skin of the donor. However, the first millilitres of blood taken, which are most likely to exhibit these foreign substances, are sent into the sampling bag rather than into the collecting bag, thereby greatly decreasing the chances of contamination of blood in the collecting bag.

Second, this arrangement makes it possible to take samples before the collecting bag is completely filled, and consequently save time.

Finally, during donation, the loss of blood volume for the donor may be compensated for by plasma. As a result, the hematocrit of the donor blood may appear artificially lower if samples are taken after the collection bag is filled.

Although this system has proven very beneficial, room for improvement remains. In one such previous system, the end part of the second tube is inserted in the inlet orifice of the sampling bag but does not enter inside the bag, or it enters only a short distance.

This presents several drawbacks due to the fact that, when the sampling bag is placed so that its inlet orifice is situated towards the top, the end of the second tube connected to the said inlet orifice is situated above the blood-air interface.

Thus, in the event of unintentional pressure on the sampling bag, the latter deforms because of its flexibility, and as a result part of the air contained in this bag rises in the tube. Because the sampling bag is connected to the collection means, there is a not insignificant risk of gas embolism, that is to say entry of air into the venous system of the donor. Additionally, it is known that an entry of air upstream of the heart may cause drainage of the heart pump and cardio-circulatory arrest, which may sometimes lead to death of the donor.

Even in the absence of unintentional pressure on the sampling bag, this configuration is not entirely satisfactory because the failure of the second tube to be immersed in the blood contained in the sampling bag (when the bag is in the aforementioned position) renders it impossible to fill tubes for analysis of the blood in the sampling bag while that bag is being filled. Instead, once the sampling bag is filled, it must be turned over so that the inlet orifice is situated downwards before samples may be removed by vacuum tube. This causes an undesired loss of time.

In another example of the previous sampling bag/collecting bag system, the end part of the second tube is inserted in the inlet orifice of the sampling bag and enters inside the bag, so that the corresponding end of the second tube is situated in the immediate vicinity of the bottom of the bag. This is in particular described in U.S. Pat. No. 6,387,086. However, this arrangement is also not fully satisfactory.

Specifically, when the bag is oriented so that the end of the tube is situated downwards, the end is in contact with the blood rather than with air very soon after blood begins to enter the sampling bag, and the embolism problems encountered with the first embodiment may be avoided. However, it is desirable to be able to place and use the sampling bag in an inverted position, where the inlet orifice is situated not towards the top but towards the bottom. This places the end of the second tube above the blood and may allow air to enter it. In this case, the system of the document U.S. Pat. No. 6,387,086 poses the same problems as those described above for the embodiment in which the second tube does not enter the sampling bag.

Moreover, in this version of the sampling bag system, the longer the end part of the second tube situated inside the sampling bag, the greater the volume of air contained in the said bag, before any collection of blood for sampling. Specifically, the volume of air is the sum of:

- the volume contained in the end part of the second tube situated inside the sampling bag; and
- the volume of air trapped around the second tube, over its entire length, between the two sheets forming the sampling bag.

Thus, the greater the length of the end part of the second tube inserted inside the bag, the greater the volume of air available to rise up in the tube as far as the vein of the donor. The risk of gas embolism is considerably increased thereby.

It is therefore particularly important to ensure that the volume of air contained inside the bag before blood donation is initiated is limited to the maximum possible extent. This is particularly true when air from a tube, such as the second tube, will be added to volume of air in the sampling bag after blood donation begins.

SUMMARY

The present invention overcomes the above or other problems with previous bag systems having a sampling bag and a collecting bag. Specifically, the present invention prevents a large volume of air from entering the vein of the donor from the bag system during donation or significantly limits the volume of air available to enter the vein of the donor. Further the present invention achieves this result regardless of the position of the sampling bag during donation or the volume of blood contained in the sampling bag.

In one embodiment, the invention includes a bag system for the collection and sampling of a biological fluid, such as blood or a blood component, from a donor. The system includes a bag for collecting the fluid and a first tube connected at a first end to collection means, such as a phlebotomy needle, and, at a second end, to an inlet orifice of the collecting bag. It also includes a flexible sampling bag defining an internal volume, the internal volume having a side forming a bottom and an introduction side opposite to the said bottom, the introduction side having an inlet orifice. Finally, the system also includes a second tube, a first end part of which is connected to the first tube at a distance from the first end of the s first tube, and a second end part of which is inserted in the inlet orifice of the sampling bag. The second end part of the second tube extends inside the sampling bag over a distance lying between 25% and 60% of the distance between the bottom side and the introduction side of the internal volume of the sampling bag.

According to a specific embodiment, the second end part of the second tube extends inside the sampling bag over a distance of between 30% and 50% of the distance between the bottom side and the introduction side of the internal volume of the sampling bag.

The bag system of some embodiments may also include a lateral sampling device connected, outside the sampling bag, to the second tube, and arranged to allow the sampling of at least part of the fluid contained in the sampling bag.

The bag system in certain embodiments may also include a set of satellite bags connected, by means of at least one tube, to at least one outlet orifice of the collecting bag. For example, the set of satellite bags may include at least two bags and a filtration unit all arranged so as to allow the circulation of the fluid in closed circuit.

BRIEF DESCRIPTION OF THE DRAWINGS

Other objects and advantages of the invention will emerge during the following description given with reference to the accompanying drawings, in which.

DETAILED DESCRIPTION

Figure 1:
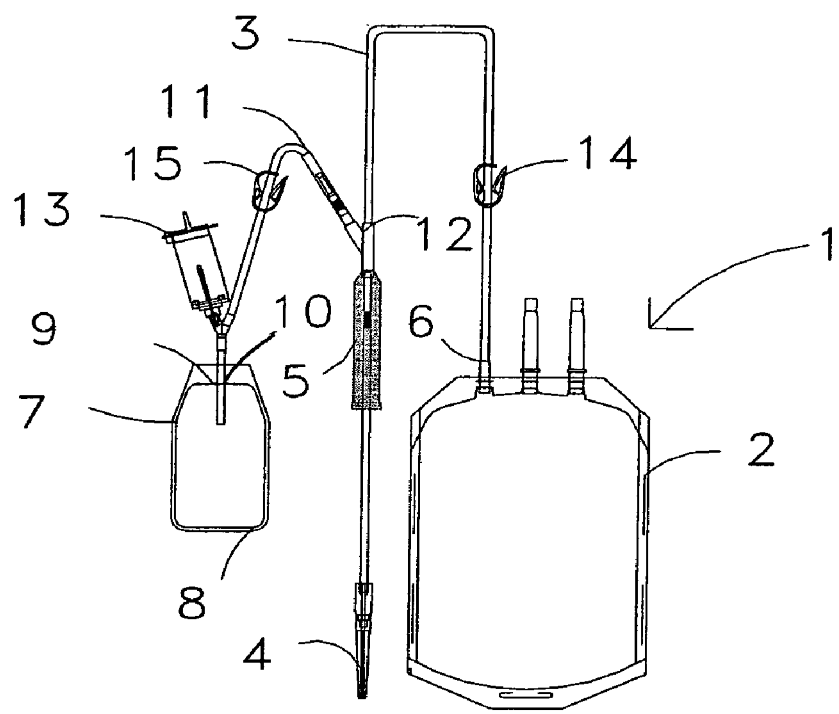
FIG. 1 is a schematic representation, in elevation, of a bag system for collection and sampling a biological fluid, according to an embodiment of the present invention, having a sampling bag provided with an inlet orifice situated towards the top.
Figure 2:
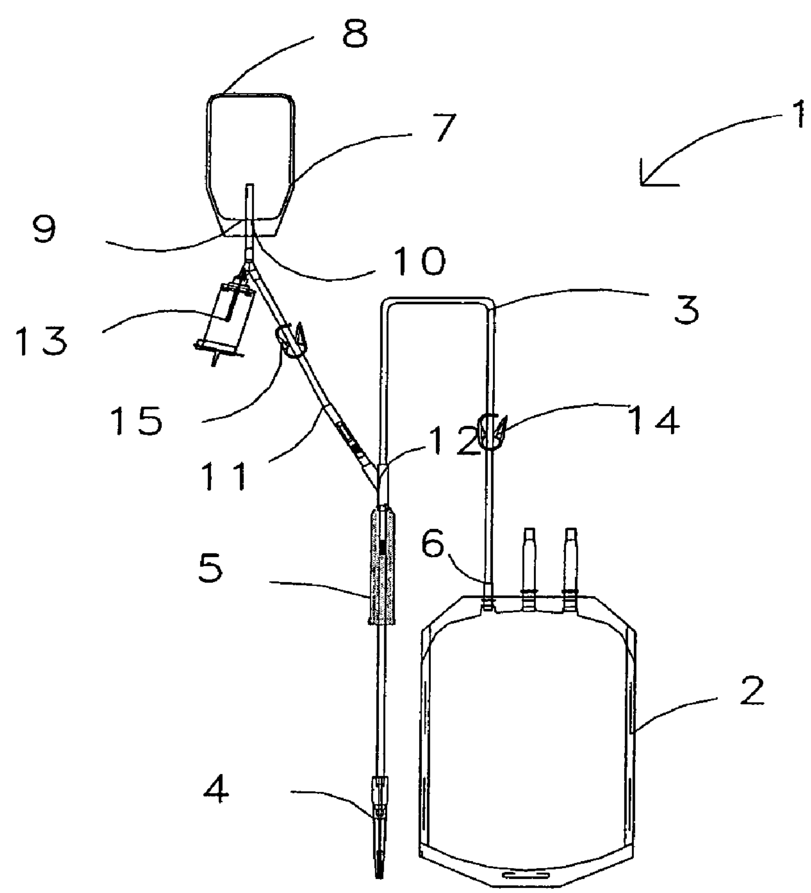
FIG. 2 is a representation similar to that in FIG. 1 with the inlet orifice of the sampling bag being situated towards the bottom.

FIGS. 1 and 2 depict a bag system 1 for collecting and sampling a biological fluid, according to one embodiment of the present invention. System 1 includes a fluid collection bag 2, a first tube 3 connected at a first end to collection means 4, and at a second end to an inlet orifice 6 of the collecting bag 2. A protector 5 for the collection means 4 may be disposed on the said tube 3.

The system 1 also includes a flexible sampling bag 7 defining an internal volume, the internal volume having a side 8 forming a bottom and an introduction side 9 opposite to the bottom side 8. The introduction side 9 has an inlet orifice 10.

The system 1 also includes a second tube 11, a first end part of which is connected, by means of a three-way junction 12, to the first tube 3, and a second end part of which is inserted in the inlet orifice 10 in the sampling bag 7.

A lateral sampling device 13 is connected, outside the sampling bag 7, to the second tube 11, and arranged to allow the collection of at least part of the fluid contained in the sampling bag 7. This lateral sampling device 13 enables the blood or other biological fluid contained in the sampling bag 7 to be collected in vacuum tubes.

Clamps 14, 15 may be placed respectively on the first 3 and second 11 tubes and make it possible to direct the blood withdrawn from the donor to the sampling bag 7 or to the collecting bag 2.

Figure 3:
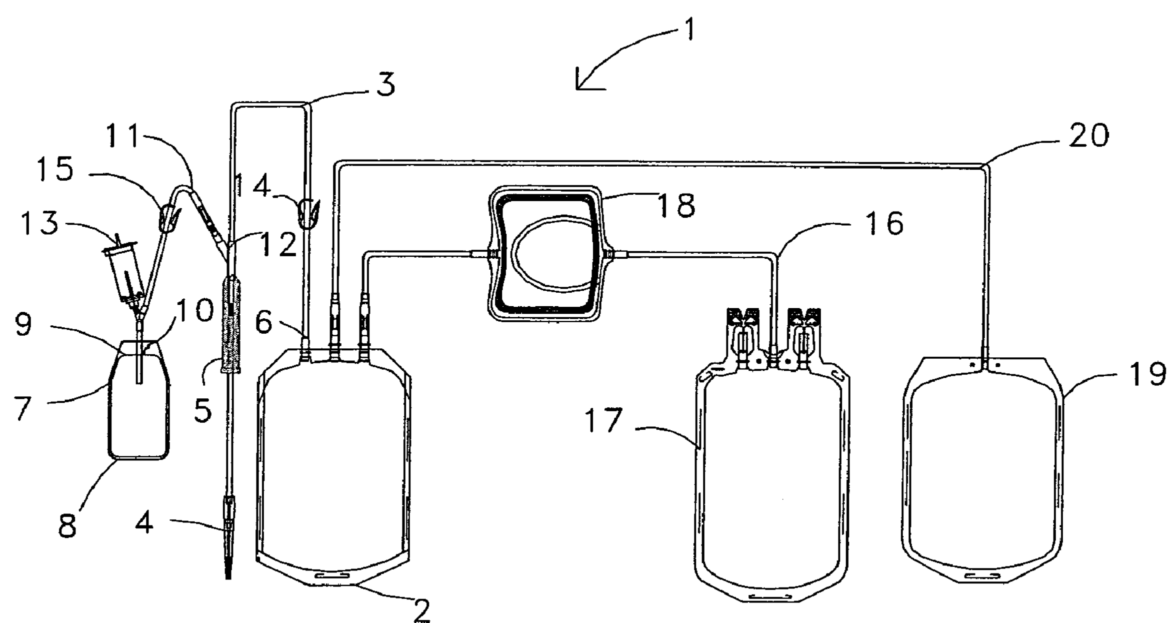
FIG. 3 is a schematic representation, in elevation, of a bag system for collecting and sampling a biological fluid, according to another embodiment of the present invention.

FIG. 3 depicts a bag system 1 for collecting and sampling a biological fluid, according to a second embodiment of the present invention. In order to perform filtration and separation steps as well as the removal of leukocytes from the various constituents of the blood, the collecting bag 2 may be in fluid communication, by means of a third tube 16, with a satellite bag 17. A filtration unit 18 for leukocyte removal may be situated between the collecting bag 2 and the satellite bag 17. The collecting bag 2 (and/or the satellite bag 17) may be in fluid communication with one or more other satellite bags 19 by means of a fourth tube 20.

In various embodiments, the bag system 1 may be arranged so as to allow the circulation of the fluid in closed circuit.

In preferred embodiments, the second end part of the second tube 11 extends inside the sampling bag 7 over a distance of between 25% and 60% of the distance between the bottom 8 and the introduction side 9 of the internal volume of the sampling bag 7.

According to one possible embodiment, the second end part of the second tube 11 extends inside the sampling bag 7 over a distance of between 30% and 50% of the distance between the bottom 8 and the introduction side 9 of the internal volume of the sampling bag 7.

Thus the end part of the second tube 11 extends inside the sampling bag 7 over a sufficient distance. Because of this, when the sampling bag is used with its inlet orifice situated towards the top (as depicted in FIG. 1), some time after donation begins, the end part of the second tube 11 is immersed in the fluid.

This makes it possible both to considerably limit the risks of gas embolism in the donor following unintentional pressure exerted on the sampling bag 7, and to allow the filling of tubes for analysis of the blood collected during the filling of the sampling bag itself or alter during the donation process.

Moreover, the end part of the second tube 11 does not extend inside the sampling bag 7 over too great a distance. Thus, when the sampling bag is used with its inlet orifice situated towards the bottom (as depicted in FIG. 2), some time after the donation begins, the end part of the second tube 11 is immersed in the fluid. As indicated previously, this reduces the risk of gas embolism for the donor but also rapidly fills the tubes for analysis of the blood collected.

In addition, because the length of the second tube 11 situated inside the sampling bag 7 is reduced, the volume of air contained in bag 7 before donation begins is also reduced. Because the volume of gas is an essential parameter in the appearance of a gas embolism, the risk of gas embolism is considerably reduced thereby.

Table 1 shows the relationship between the volume of gas able to move through the tube 11 as far as the vein of the donor and the length of the portion of tube 11 extending within sampling bag 7.

TABLE 1

Correlation of Second Tube Length and Volume of Air Able to Enter Vein of Donor

| | Length of tube (cm) | Volume of air (ml) | Length of tube (cm) | Volume of air (ml) | Length of tube (cm) | Volume of air (ml) |
|---|---|---|---|---|---|---|
| Test N° 1 | 2 | 5 | 5 | 8 | 10 | 10 |
| Test N° 2 | 2 | 6 | 5 | 8 | 10 | 11 |
| Test N° 3 | 2 | 6 | 5 | 8 | 10 | 11 |
| Test N° 4 | 2 | 5 | 5 | 8 | 10 | 11 |
| Mean | 2 | 5.5 | 5 | 8 | 10 | 10.75 |

The lengths of tube used in this test (2, 5 and 10 cm) correspond respectively to a percentage of 19, 48 and 95% with respect to the length of the bag 7 used in these tests.

The characteristics of this bag 7 were as follows:

length: 10.5 cm;

width: 5 cm;

volume: 40 ml.

In order to avoid the drawbacks arising when the tube 11 does not enter or enters very little within the sample bag 7, while still limiting the volume of air contained in the bag 7, it is preferable for the end part of the second tube 11 to extend inside the sampling bag 7 over a distance of between 25% and 60% of the distance between the bottom 8 and the introduction side 9 of the internal volume of the sampling bag 7.

Thus the invention considerably limits the risks of gas embolism whatever the preferred position in which the sampling bag 7 is used, particularly in the embodiments shown in FIGS. 1 and 2. Additionally, by limiting the volume of air able to enter the vein of the donor, embodiments of the present invention may decrease the amount of harm to the donor should an embolism occur.

Although the present invention and its advantages have been described in detail, it should be understood that various changes, substitutions and alterations can be made herein without departing from the spirit and scope of the invention as defined by the following claims.

The invention claimed is:

1. A bag system for collecting and sampling a biological fluid from a donor comprising:

a collection bag for collecting the biological fluid;

a first tube connected at a first end to a collection means and at a second end to the collection bag;

a flexible sampling bag defining an internal volume, the internal volume having a bottom side and an introduction side having an inlet orifice;

a second tube having a first end connected to the first tube and a second end inserted into the inlet orifice of the sampling bag; and a lateral sampling device connected to the second tube outside of the sampling bag and operable to allow the collection of biological fluid samples from the sampling bag, wherein the second end of the second tube extends into the internal volume of the sampling bag over a distance between 25% and 60% of the distance between the bottom side and the introduction side of the internal volume.

2. A bag system for collecting and sampling a biological fluid from a donor comprising:

a collection bag for collecting the biological fluid;

a first tube connected at a first end to a collection means and at a second end to the collection bag;

a flexible sampling bag defining an internal volume, the internal volume having a bottom side and an introduction side having an inlet orifice; and a second tube having a first end connected to the first tube and a second end inserted into the inlet orifice of the sampling bag, wherein the second end of the second tube extends into the internal volume of the sampling bag over a distance between 25% and 60% of the distance between the bottom side and the introduction side of the internal volume; and wherein the biological fluid comprises blood or a blood component.

3. The bag system of claim 2, further comprising the system operable to reduce the risk of embolism to the donor during donation of the blood or blood component.

4. A bag system for collecting and sampling a biological fluid from a donor comprising:

a collection bag for collecting the biological fluid;

a first tube connected at a first end to a collection means and at a second end to the collection bag;

a flexible sampling bag defining an internal volume, the internal volume having a bottom side and an introduction side having an inlet orifice;

a second tube having a first end connected to the first tube and a second end inserted into the inlet orifice of the sampling bag, wherein the second end of the second tube extends into the internal volume of the sampling bag over a distance between 25% and 60% of the distance between the bottom side and the introduction side of the internal volume;

a satellite bag system;

at least one satellite tube connected at a first end to the satellite bag system and connected at a second end to the collecting bag; and a lateral sampling device connected to the second tube outside of the sampling bag and operable to allow the collection of biological fluid samples from the sampling bag.

5. A bag system for collecting and sampling a biological fluid from a donor comprising:

a collection bag for collecting the biological fluid;

a first tube connected at a first end to a collection means and at a second end to the collection bag;

a flexible sampling bag defining an internal volume, the internal volume having a bottom side and an introduction side having an inlet orifice;

a second tube having a first end connected to the first tube and a second end inserted into the inlet orifice of the sampling bag, wherein the second end of the second tube extends into the internal volume of the sampling bag over a distance between 25% and 60% of the distance between the bottom side and the introduction side of the internal volume;

a satellite bag system;

at least one satellite tube connected at a first end to the satellite bag system and connected at a second end to the collecting bag;

wherein the biological fluid comprises blood or a blood component.

6. The bag system of claim 5, further comprising the system operable to reduce the risk of embolism to the donor during donation of the blood or blood component.

* * * * *